United States Patent [19]

Lemelson

[11] 4,285,338
[45] Aug. 25, 1981

[54] ADHESIVE BANDAGE

[76] Inventor: Jerome H. Lemelson, 85 Rector St., Metuchen, N.J. 08840

[21] Appl. No.: 80,565

[22] Filed: Oct. 1, 1979

[51] Int. Cl.³ .............................................. A61F 13/00
[52] U.S. Cl. .................................................... 128/155
[58] Field of Search ............ 128/155, 156, 154, 132 R, 128/268

[56] References Cited

U.S. PATENT DOCUMENTS

| 2,443,140 | 6/1948 | Larsen ................... 128/154 |
| 3,416,525 | 12/1968 | Yeremian ............. 128/268 X |
| 4,023,569 | 5/1977 | Warnecke et al. ..... 128/154 |
| 4,212,296 | 7/1980 | Schaar ................... 128/156 |

Primary Examiner—John D. Yasko

[57] ABSTRACT

An adhesive bandage for covering and protecting a wound. In one form, the bandage is composed of a patch or strip of adhesive tape having a gauze section attached to its central portion and a hollow rigid shell of plastic attached to the outside of the central portion for protecting a wound against forces applied thereto. For providing a novelty effect, the shell may contain an exterior illustration or may be irregularly formed to simulate a face or mock character. In another form, the shell may be formed of a resilient plastic resin which will absorb shock and impact to protect the wound.

10 Claims, 5 Drawing Figures

ADHESIVE BANDAGE

SUMMARY OF THE INVENTION

This invention relates to improvements in dressings and adhesive bandages used to cover and protect wounds, such as cuts, abrasions, punctures and other forms of wounds inflicted on human tissue such as the skin of the arms, legs, hands and other parts of the human body. In particular, the invention is directed to preformed bandages which are adhesively retained against the skin and which contain, in addition to a soft absorbant material such as gauze, adapted to be disposed against or above a body wound, a self supporting shell formed of a substantially more rigid plastic then the plastic of which the adhesive tape is formed. The shell includes a central dome-like portion which protrudes a distance above the central portion of the bandage and therefor provides a protective roof or cup-like cover above the bandage, which will prevent the direct engagement of any surface against which the wounded portion of the person wearing the bandage may engage or unintentionally strike. The shell-like portion of the bandage assembly preferably contains one or more flange portions which are bonded or welded to the inner portions of the extremities of the tape defining the bandage may be formed of vacuum formed rigid plastic sheets or injection molded plastic. The outer surface of the shell may be specially decorated and/or irregularly configured to serve as a novelty arrangement and incentive for children to wear the bandage. The inside of the shell may contain a resilient material, such as a flexible cellular plastic resin, which serves to further absorb shock and protect the wound.

The conventional adhesive bandage which is employed to cover a cut or other type of wound in the skin is composed of a strip of adhesive tape having a shorter strip of gauze attached to its central portion. While such a bandage serves the purpose of covering and protecting the wound from dirt and foreign material, it does not serve to protect the wound from impact with foreign bodies, as may be frequently experienced when the person wearing the bandage has the limb or other portion of the body suddenly engaged by or engages a hard surface. When such impact is experienced, the wearer of the bandage may experience pain and the wound may be opened or the clotted blood thereof ruptured or broken. The instant invention is directed to a structure and an adhesive bandage for preventing further injury to a wound due to certain types of impact of the wound with a foreign body.

Accordingly it is a primary object of this invention to provide a new and improved structure in an adhesive bandage.

Another object is to provide an adhesive bandage which includes shock absorbing means for impact forces applied thereto.

Another object is to provide an adhesive bandage containing a lightweight shell extending over and across the wound covering portion of the bandage for protecting the wound against direct impact of the bandage with foreign objects.

Another object is to provide an adhesive bandage containing a protective cover for the wound engaging portion of the bandage, which cover may be illustrated and decorated to improve the appearance of the bandage.

Another object is to provide an adhesive bandage having a protective cover for the wound covering portion of the bandage, which cover is molded to an irregular shape.

Another object is to provide an adhesive bandage with a protective cover portion shaped to represent a mock figure or head, thereby rendering the bandage attractive to children.

With the above and such other objects in view as may hereinafter more fully appear, the invention consists of the novel constructions, combinations and arrangements of parts as will be more fully described and illustrated in the accompanying drawings, but it is to be understood that changes, variations and modifications may be resorted to which fall within the scope of the invention as claimed.

Figure 1:
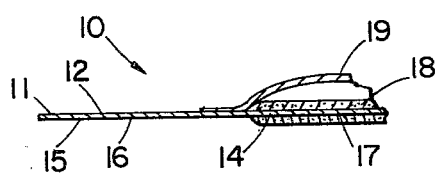
FIG. 1 is a side view in cross section of a portion of a bandage employed for application to light flesh wounds and burns and having a protective dome-shaped device attached thereto.
Figure 2:
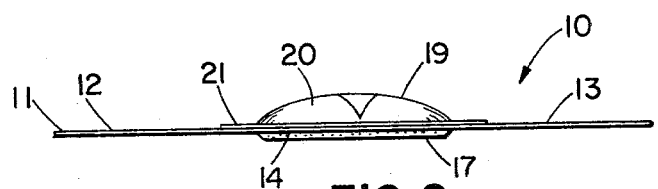
FIG. 2 is a side view of the device of FIG. 1.
Figure 3:
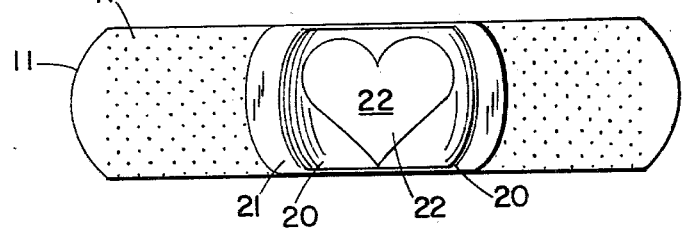
FIG. 3 is a top view of the device of FIG. 2.

In FIGS. 1 to 3 is shown an adhesive bandage 10 formed of a flat strip 11 of flexible adhesive tape, such as a strip of plastic sheet or film or impregnated cloth, having end portions 12 and 13 extending from both ends of a central portion 14. The bottom surface 15 of the end portions 12 and 13 is coated with an adhesive 16 and covered with respective peelable protective plastic strips [not shown] of film such as polyethylene film. Bonded or welded above the central portion 14 are the end flanges 21A and 21B of a rigid plastic shell 19 having dome-like cover portion 20 formed integral with the flanges and disposed over and above the central portion 14 of the tape 11 and in direct alignment with a patch 17 of gauze or absorbant material which is adapted to lie directly against a wound covered by the bandage. The dome-like cover 20 is preferably formed of a rigid plastic material, such as high density polyethylene, polypropylene, rigid polyvinyl chloride, polystyrene, cellulose acetate or any other suitable rigid plastic. The dome portion 20 serves to protect the skin wound against injury caused when the portion of the body containing the wound strikes an object or is struck by a foreign body. Flanges 21A and 21B are heat sealed, electronically sealed or adhesive bonded to the top surface 12 of the tape.

Notation 18 refers to a resilient pad of flexible plastic foam bonded to the top surface of the central portion 14 of the tape inside the dome 20 for further protecting the wound. Such flexible plastic foam or other shock absorbing material may completely fill the inside volume between the dome portion 20 and the top surface 12 of the tape 15.

Notation 16 refers to adhesive material coating the underside of the tape while notation 21 refers to the upper surface of the dome 20 and 22 refers to a printed illustration provided on such upper surface.

Figure 4:
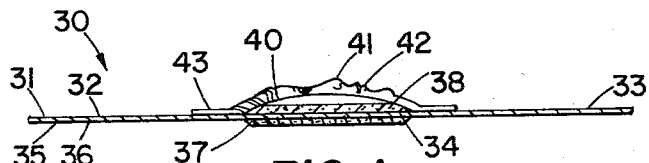
FIG. 4 is a side view in cross section of a modified form of bandage of the type shown in FIG. 1 wherein the dome shaped protector is molded with a novelty configuration.
Figure 5:
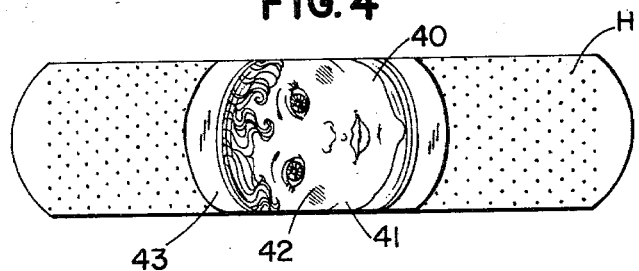
FIG. 5 is a top view of the bandage of FIG. 4.

In FIGS. 4 and 5 is shown a modified form of the adhesive bandage illustrated in FIGS. 1–3. The bandage assembly 30 is formed of an elongated strip 31 of flexible plastic having holes H perforated in the end portions 32 and 33 thereof for allowing perspiration to evaporate. The bottom surface 35 of the tape 31 is coated with an adhesive 36 along the end portions 32 and 33 thereof while the central portion 34 contains gauze or other flexible absorbant material attached thereto by adhesive. The upper surface of the central portion 34 has a dome-like portion 41 of a vacuum formed or injection molded flange rigid member 40, the flanges 43 and 44 of which are adhesively bonded or heat sealed to the upper surface of the tape 31 as described. The device 40 differs from that which is illustrated in FIGS. 1-3 in that the upper surface of the central portion 41 is irregularly shaped with irregularities 42, such as the portions of a mock face illustrated in FIGS. 4 and 5, giving a three dimensional effect and further rigidizing the dome shaped portion to improve its ability to absorb shock and prevent direct contact with the material therebeneath which contacts the wound. Notation 38 refers to a resilient material, such as flexible plastic foam, filling or partially filling the interior of the dome shaped portion 41 of device 40.

I claim:

1. An adhesive bandage comprising in combination: an elongated thin strip of flexible bandage material containing end portions for engagement with the skin of a person using said bandage and adhesive material coating the inside surfaces of said end portions for adhering said end portions to portions of the skin, a central portion of said bandage containing soft material and void of such adhesive, and a protecting member made of a molded plastic resinous material, said protecting member being more rigid in structure than said thin strip of flexible material and having an irregular external surface, said protecting member defining the outer wall of the central portion of said bandage and protruding outwardly from said central portion of said elongated flexible thin strip, said protecting member being integrally bonded to the outer surface of said elongated thin strip intermediate the ends thereof, said protecting member serving as a cover and shock absorbing means for protecting the wound covered by the central portion of the bandage.

2. An adhesive bandage in accordance with claim 1 wherein said irregularly shaped plastic member is a shell formed of thin, rigid plastic material.

3. An adhesive bandage in accordance with claim 2 wherein said shell has an arcuate, dome-like configuration.

4. An adhesive bandage in accordance with claim 2 wherein said shell has a decoration provided on its outer surface.

5. An adhesive bandage in accordance with claim 2 wherein said shell is molded with an irregular central configuration.

6. An adhesive bandage in accordance with claim 5 wherein said irregular configuration is shaped to represent portions of the face of a mock head.

7. An adhesive bandage in accordance with claim 2 including respective opposite flange portions extending from said irregular portion of said shell, said flange portions being adhesively bonded to respective portions of said flexible adhesive tape to retain the shell thereon.

8. An adhesive bandage in accordance with claim 6, said protecting member having respective end flange portions disposed against the upper surface of said elongated flexible thin strip and being electronically heat sealed thereto.

9. An adhesive bandage in accordance with claim 1 wherein said molded plastic member protecting said central portion of said bandage is injection molded of a plastic resin and bonded to the outer surface of said elongated flexible thin strip.

10. An adhesive bandage in accordance with claim 1 including a resilient, shock absorbing material at least partially filling the interior of said plastic protecting member.

* * * * *